US011707323B2

(12) United States Patent
Schultheis et al.

(10) Patent No.: US 11,707,323 B2
(45) Date of Patent: Jul. 25, 2023

(54) ELECTRICAL ANALYZER ASSEMBLY FOR INTRAVASCULAR LITHOTRIPSY DEVICE

(71) Applicant: Bolt Medical, Inc., Carlsbad, CA (US)

(72) Inventors: Eric Schultheis, San Clemente, CA (US); Gerald D. Bacher, Carlsbad, CA (US)

(73) Assignee: BOLT MEDICAL, INC., Carlsbad, CA (US)

( * ) Notice: Subject to any disclaimer, the term of this patent is extended or adjusted under 35 U.S.C. 154(b) by 137 days.

(21) Appl. No.: 17/211,150

(22) Filed: Mar. 24, 2021

(65) Prior Publication Data

US 2021/0307828 A1    Oct. 7, 2021

Related U.S. Application Data

(60) Provisional application No. 63/004,977, filed on Apr. 3, 2020.

(51) Int. Cl.
*A61B 18/24* (2006.01)
*A61B 17/00* (2006.01)
*A61B 18/00* (2006.01)

(52) U.S. Cl.
CPC .. *A61B 18/245* (2013.01); *A61B 2017/00026* (2013.01); *A61B 2017/00039* (2013.01);
(Continued)

(58) Field of Classification Search
CPC ........ A61B 18/245; A61B 2017/00026; A61B 2017/00039; A61B 2017/00154; A61B 2018/0022
See application file for complete search history.

(56) References Cited

U.S. PATENT DOCUMENTS

| | | |
|---|---|---|
| 4,649,924 A | 3/1987 | Taccardi |
| 4,699,147 A | 10/1987 | Chilson et al. |

(Continued)

FOREIGN PATENT DOCUMENTS

| | | |
|---|---|---|
| AU | 2017205323 | 1/2022 |
| AU | 2019452180 | 1/2022 |

(Continued)

OTHER PUBLICATIONS

International Search Report and Written Opinion dated Nov. 8, 2022 in PCT Application Serial No. PCT US/2022/039678.

(Continued)

*Primary Examiner* — Carl H Layno
*Assistant Examiner* — Aya Ziad Bakkar
(74) *Attorney, Agent, or Firm* — Roeder & Broder LLP; James P. Broder

(57) ABSTRACT

A catheter system for treating a treatment site within or adjacent to a vessel wall or a heart valve includes an energy source, a balloon, an energy guide, and an electrical analyzer assembly. The energy source generates energy. The balloon is positionable substantially adjacent to the treatment site. The balloon has a balloon wall that defines a balloon interior that receives a balloon fluid. The energy guide is configured to receive energy from the energy source and guide the energy into the balloon interior. The electrical analyzer assembly is configured to monitor a balloon condition during use of the catheter system. The electrical analyzer assembly can include a first electrode, a second electrode, and an impedance detector that is electrically coupled to the first electrode and the second electrode. The impedance detector is configured to detect impedance between the first electrode and the second electrode.

20 Claims, 6 Drawing Sheets

(52) U.S. Cl.
 CPC ............... *A61B 2017/00154* (2013.01); *A61B 2018/0022* (2013.01)

(56) References Cited

U.S. PATENT DOCUMENTS

| | | | |
|---|---|---|---|
| 4,799,479 A | 1/1989 | Spears | |
| 4,913,142 A | 4/1990 | Kittrell et al. | |
| 4,955,895 A | 9/1990 | Sugiyama | |
| 4,960,108 A | 10/1990 | Reichel et al. | |
| 4,994,059 A | 2/1991 | Kosa et al. | |
| 5,034,010 A | 7/1991 | Kittrell et al. | |
| 5,041,121 A | 8/1991 | Wondrazek et al. | |
| 5,104,391 A | 4/1992 | Ingle | |
| 5,116,227 A | 5/1992 | Levy | |
| 5,152,768 A | 10/1992 | Bhatta | |
| 5,173,049 A | 12/1992 | Levy | |
| 5,181,921 A | 1/1993 | Makita et al. | |
| 5,200,838 A | 4/1993 | Nudelman | |
| 5,290,277 A | 3/1994 | Vercimak et al. | |
| 5,372,138 A | 12/1994 | Crowley | |
| 5,400,428 A | 3/1995 | Grace | |
| 5,422,926 A | 6/1995 | Smith | |
| 5,454,809 A | 10/1995 | Janssen | |
| 5,509,917 A | 4/1996 | Cecchetti | |
| 5,540,679 A | 7/1996 | Fram | |
| 5,562,657 A | 10/1996 | Griffin | |
| 5,598,494 A | 1/1997 | Behrmann et al. | |
| 5,609,606 A | 3/1997 | O'Boyle | |
| 5,611,807 A | 3/1997 | O'Boyle | |
| 5,697,377 A | 12/1997 | Wittkamph | |
| 5,718,241 A | 2/1998 | Ben-Haim et al. | |
| 5,729,583 A | 3/1998 | Tang | |
| 5,772,609 A | 6/1998 | Nguyen et al. | |
| 5,891,135 A | 4/1999 | Jackson et al. | |
| 5,906,611 A | 5/1999 | Dodick et al. | |
| 5,944,697 A | 8/1999 | Benett et al. | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,203,537 B1 | 3/2001 | Adrian | |
| 6,210,404 B1 | 4/2001 | Shadduck | |
| 6,339,470 B1 | 1/2002 | Papademetriou et al. | |
| 6,368,318 B1 | 4/2002 | Visuri et al. | |
| 6,500,174 B1 | 12/2002 | Maguire et al. | |
| 6,514,203 B2 | 2/2003 | Bukshpan | |
| 6,514,249 B1 | 2/2003 | Maguire et al. | |
| 6,524,251 B2 | 3/2003 | Rabiner et al. | |
| 6,538,739 B1 | 3/2003 | Visuri et al. | |
| 6,607,502 B1 | 8/2003 | Maguire et al. | |
| 6,652,547 B2 | 11/2003 | Rabiner et al. | |
| 6,666,834 B2 | 12/2003 | Restle et al. | |
| 6,773,447 B2 | 8/2004 | Laguna | |
| 6,849,994 B1 | 2/2005 | White et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,309,324 B2 | 12/2007 | Hayes et al. | |
| 7,470,240 B2 | 12/2008 | Schultheiss et al. | |
| 7,569,032 B2 | 8/2009 | Naimark et al. | |
| 7,599,588 B2 | 10/2009 | Eberle et al. | |
| 7,713,260 B2 | 5/2010 | Lessard | |
| 7,758,572 B2 | 7/2010 | Weber et al. | |
| 7,810,395 B2 | 10/2010 | Zhou | |
| 7,850,685 B2 | 12/2010 | Kunis et al. | |
| 7,867,178 B2 | 1/2011 | Simnacher | |
| 7,972,299 B2 | 7/2011 | Carter | |
| 7,985,189 B1 | 7/2011 | Ogden et al. | |
| 8,162,859 B2 | 4/2012 | Schultheiss et al. | |
| 8,166,825 B2 | 5/2012 | Zhou | |
| 8,192,368 B2 | 6/2012 | Woodruff | |
| 8,292,913 B2 | 10/2012 | Warnack | |
| 8,364,235 B2 | 1/2013 | Kordis et al. | |
| 8,419,613 B2 | 4/2013 | Saadat | |
| 8,439,890 B2 | 5/2013 | Beyar | |
| 8,556,813 B2 | 10/2013 | Cashman et al. | |
| 8,574,247 B2 | 11/2013 | Adams et al. | |
| 8,657,814 B2 | 2/2014 | Werneth | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 8,986,339 B2 | 3/2015 | Warnack | |
| 8,992,817 B2 | 3/2015 | Stamberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,289,132 B2 | 3/2016 | Ghaffari et al. | |
| 9,289,224 B2 | 3/2016 | Adams et al. | |
| 9,320,530 B2 | 4/2016 | Grace | |
| 9,333,000 B2 | 5/2016 | Hakala et al. | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,730,715 B2 | 8/2017 | Adams | |
| 9,764,142 B2 | 9/2017 | Imran | |
| 9,814,476 B2 | 11/2017 | Adams et al. | |
| 9,861,377 B2 | 1/2018 | Mantell et al. | |
| 9,867,629 B2 | 1/2018 | Hawkins et al. | |
| 9,894,756 B2 | 2/2018 | Weinkam et al. | |
| 9,955,946 B2 | 5/2018 | Miller et al. | |
| 9,974,963 B2 | 5/2018 | Imran | |
| 9,974,970 B2 | 5/2018 | Nuta | |
| 9,993,292 B2 | 6/2018 | Adams et al. | |
| 10,039,561 B2 | 8/2018 | Adams et al. | |
| 10,136,829 B2 | 11/2018 | Deno et al. | |
| 10,149,690 B2 | 12/2018 | Hawkins et al. | |
| 10,159,505 B2 | 12/2018 | Hakala et al. | |
| 10,194,994 B2 | 2/2019 | Deno et al. | |
| 10,201,387 B2 | 2/2019 | Grace et al. | |
| 10,206,698 B2 | 2/2019 | Hakala et al. | |
| 10,226,265 B2 | 3/2019 | Ku et al. | |
| 10,357,264 B2 | 7/2019 | Kat-Kuoy | |
| 10,405,923 B2 | 9/2019 | Yu et al. | |
| 10,406,031 B2 | 9/2019 | Thyzel | |
| 10,420,569 B2 | 9/2019 | Adams | |
| 10,441,300 B2 | 10/2019 | Hawkins | |
| 10,478,202 B2 | 11/2019 | Adams et al. | |
| 10,517,620 B2 | 12/2019 | Adams | |
| 10,517,621 B1 | 12/2019 | Hakala et al. | |
| 10,537,287 B2 | 1/2020 | Braido et al. | |
| 10,555,744 B2 | 2/2020 | Nguyen et al. | |
| 10,561,428 B2 | 2/2020 | Eggert et al. | |
| 10,646,240 B2 | 5/2020 | Betelia et al. | |
| 10,682,178 B2 | 6/2020 | Adams et al. | |
| 10,702,293 B2 | 7/2020 | Adams et al. | |
| 10,709,462 B2 | 7/2020 | Nguyen et al. | |
| 10,758,255 B2 | 9/2020 | Adams | |
| 10,842,567 B2 | 11/2020 | Grace et al. | |
| 10,959,743 B2 | 3/2021 | Adams et al. | |
| 10,966,737 B2 | 4/2021 | Nguyen | |
| 10,967,156 B2 | 4/2021 | Gulachenski | |

(56) References Cited

U.S. PATENT DOCUMENTS

| | | |
|---|---|---|
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0060990 A1 | 3/2007 | Satake |
| 2007/0088380 A1 | 4/2007 | Hirszowicz et al. |
| 2007/0118057 A1 | 5/2007 | Ein-Gal |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1* | 9/2012 | Stahmann ............ A61B 5/026 600/483 |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0116714 A1 | 5/2013 | Adams et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0180069 A1 | 6/2014 | Millett |
| 2014/0180126 A1 | 6/2014 | Millett |
| 2014/0180134 A1 | 6/2014 | Hoseit |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0336632 A1 | 11/2014 | Toth |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0276689 A1 | 10/2015 | Watanabe et al. |

(56) References Cited

U.S. PATENT DOCUMENTS

| | | |
|---|---|---|
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-kuoy |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0104933 A1 | 4/2019 | Stern |
| 2019/0175111 A1 | 6/2019 | Genereux et al. |
| 2019/0175300 A1 | 6/2019 | Horn |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0388002 A1 | 12/2019 | Bozsak et al. |
| 2019/0388110 A1 | 12/2019 | Nguyen et al. |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1* | 1/2020 | Cottone ............. A61B 17/0218 |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0129195 A1 | 4/2020 | McGowan et al. |
| 2020/0129741 A1 | 4/2020 | Kawwas |
| 2020/0197019 A1 | 6/2020 | Harper |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |

(56) References Cited

FOREIGN PATENT DOCUMENTS

| | | |
|---|---|---|
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A1 | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0119296 A1 * | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | 9902095 A1 | 1/1999 |
| WO | 1999002095 A1 | 1/1999 |
| WO | 9920189 A1 | 4/1999 |
| WO | 1999020189 A1 | 4/1999 |
| WO | WO200067648 | 11/2000 |
| WO | WO2000067648 A1 | 11/2000 |
| WO | WO0103599 A2 | 1/2001 |
| WO | 20060006169 A2 | 1/2006 |
| WO | WO2009121017 | 10/2009 |
| WO | WO2009149321 A1 | 12/2009 |
| WO | 2010042653 A1 | 4/2010 |
| WO | WO2011094379 | 8/2011 |
| WO | 20110126580 A2 | 10/2011 |
| WO | WO2012025833 | 3/2012 |
| WO | WO20120052924 A1 | 4/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 201501///90 A1 | 11/2015 |
| WO | WO2016089683 A1 | 6/2016 |
| WO | WO2016090175 | 6/2016 |
| WO | WO2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021067563 | 4/2021 |
| WO | WO2021086571 A1 | 5/2021 |
| WO | WO2021096922 A1 | 5/2021 |
| WO | WO2021101766 A1 | 5/2021 |
| WO | WO2021126762 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015.
Medlight, "Cylindircal light diffuser Model RD", Medlight S.A., Switzerland. 2015.
Ohl, Siew-Wan, et al. "Bubbles with shock waves and ultrasound: a review", Interface Focus, pp. 1-15, vol. 5, The Royal Society Publishing Oct. 2015.
Schafter+Kirchhoff, Laser Beam Couplers series 60SMS for coupling into single-mode and polarization-maintaining fiber cables, Schafter+Kirchhoff, pp. 1-5, Germany. Dec. 2, 2021.
Meng et al., "Accurate Recovery of Atrial Endocardial Potential Maps From Non-contact Electrode Data." Auckland Bioengineering Institute. (ID 1421). May 2019.

(56) References Cited

OTHER PUBLICATIONS

Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.

Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

Mcateer, James A., et al. "Ultracal-30 Gypsum Arlilicial Stones for Research on the Mechinisms of Stone Breakage in Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland.

Medlight, "Cylindircal light diffuser Model RD", Medlight S.A., Switzerland.

Mayo, Michael E., "Interaction of Laser Radiation with Urinary Calculi", Cranfield University Defense and Security, PhD Thesis, 2009, Cranfield University.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'Nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing.

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologies, 2014, Pinnacle Biologies, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

(56) References Cited

OTHER PUBLICATIONS

Hui, C., et al. "Research on sound fields generated by laser-induced liquid breakdown", Optica Applicata, 2010, pp. 398-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion, issued by the European Patent Office for PCT/2021/XXX, dated Sep. 30, 2021.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.

(56) References Cited

OTHER PUBLICATIONS

Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, dated Jan. 16, 2019.
European Search Report, for European Patent Application No. 18185152.8, dated Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/ US2022/015577.
International Search Report and Written Opinion dated May 13, 2022 in PCT Application Serial No. PCT/US2022/017562.
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
International Search Report and Written Opinion dated Aug. 20, 2021 in PCT Application Serial No. PCT/US2021/031130.
International Search Report and Written Opinion, issued by the EP/ISA, in PCT/US2021/048819, dated Jan. 14, 2022.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillei Ie, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and ShockWaves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Ostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and on Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.

(56) References Cited

OTHER PUBLICATIONS

Vogel, A et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method for Fabricating Artificial Kidney Stones of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421).
Jiang et al., "Multielectrode Catheter for Substrate MappingfFor Scar-related VT Ablation: A Comparison Between Grid Versus Linear Configurations." UChicago Medicine, Center for Arrhythmia Care, Chicago IL (ID 1368).
Sacher et al., "Comparison of Manual Vs Automatic Annotation to Identify Abnormal Substrate for Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion, PCT Application Serial No. PCT/US2022/047751 dated Feb. 10, 2023, by the European Patent Office.

* cited by examiner

ELECTRICAL ANALYZER ASSEMBLY FOR INTRAVASCULAR LITHOTRIPSY DEVICE

RELATED APPLICATION

This application claims priority on U.S. Provisional Application Ser. No. 63/004,977, filed on Apr. 3, 2020. To the extent permitted, the contents of U.S. Provisional Application Ser. No. 63/004,977 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a catheter system for placement within a blood vessel having a vessel wall. The catheter system can be used for treating a treatment site within or adjacent to the vessel wall. In various embodiments, the catheter system includes an energy source, a balloon, an energy guide, and an electrical analyzer assembly. The energy source generates energy. The balloon is positionable substantially adjacent to the treatment site. The balloon has a balloon wall that defines a balloon interior. The balloon interior receives a balloon fluid. The energy guide is configured to receive energy from the energy source and guide the energy into the balloon interior. The electrical analyzer assembly is configured to monitor a balloon condition during use of the catheter system.

In some embodiments, the electrical analyzer assembly analyzes an electrical signal and determines the balloon condition based at least in part on the electrical signal. For example, in certain such embodiments, the electrical analyzer assembly analyzes the electrical signal and determines a rupture of the balloon based at least in part on the electrical signal.

In various embodiments, the electrical analyzer assembly includes a first electrode, a second electrode, and an impedance detector that is electrically coupled to the first electrode and the second electrode. In such embodiments, the impedance detector is configured to detect impedance between the first electrode and the second electrode.

In some embodiments, the first electrode is positioned in a manner to be in communication with the balloon fluid within the balloon interior; and the second electrode is positioned in a manner to not be in communication with the balloon fluid within the balloon interior. More particularly, in such embodiments, the second electrode can be positioned in a manner to be in communication with blood of the patient with no nonconductive materials positioned between the second electrode and the blood of the patient.

In certain embodiments, the impedance detector generates a detector signal based at least in part on the detected impedance between the first electrode and the second electrode.

In some embodiments, the catheter system further includes a system controller that is electrically coupled to the impedance detector. The system controller is configured to receive the detector signal from the impedance detector and to determine the balloon condition based at least in part on the detector signal. In alternative embodiments, the impedance detector can be electrically coupled to the system controller via a wired connection, or the impedance detector can be electrically coupled to the system controller via a wireless connection.

In various embodiments, the system controller is configured to recognize a normal balloon condition based at least in part on the detector signal. Additionally, in certain embodiments, the system controller is configured to recognize a potential rupture of the balloon based at least in part on the detector signal. Further, in such embodiments, the system controller can be configured to automatically shut down operation of the catheter system upon recognition of the potential rupture of the balloon.

In certain embodiments, the first electrode is positioned within the balloon interior. Alternatively, in other embodiments, the catheter system further includes an inflation conduit through which the balloon fluid is directed into the balloon interior; and the first electrode can be positioned within the inflation conduit.

In some embodiments, the second electrode is positioned on skin of the patient. Alternatively, in other embodiments, the catheter system further includes a guidewire that is configured to guide positioning of the balloon substantially adjacent to the treatment site; and the second electrode can be positioned substantially adjacent to the guidewire. Still alternatively, in still other embodiments, the catheter system further includes a guidewire that is configured to guide positioning of the balloon substantially adjacent to the treatment site, and a guidewire lumen that is configured to move over the guidewire, the guidewire lumen being coupled to the balloon; and the second electrode can be positioned within the guidewire lumen.

In certain embodiments, the energy source generates pulses of energy that are guided along the energy guide into the balloon interior to induce plasma formation in the balloon fluid within the balloon interior. Further, in such embodiments, the plasma formation can cause rapid bubble formation and imparts pressure waves upon the balloon wall adjacent to the treatment site.

In some embodiments, the energy source is a laser source that provides pulses of laser energy.

In certain embodiments, the energy guide includes an optical fiber.

In various embodiments, the energy source is a high voltage energy source that provides pulses of high voltage.

In certain embodiments, the energy guide can include an electrode pair including spaced apart electrodes that extend into the balloon interior; and pulses of high voltage from the energy source can be applied to the electrodes and form an electrical arc across the electrodes.

The present invention is also directed toward a method for treating a treatment site within or adjacent to a vessel wall within a body of a patient, the method including the steps of generating energy with an energy source; positioning a balloon substantially adjacent to the treatment site, the balloon having a balloon wall that defines a balloon interior that receives a balloon fluid; receiving energy from the energy source with an energy guide; guiding the energy with the energy guide into the balloon interior; and monitoring a balloon condition with an electrical analyzer assembly while energy is being guided into the balloon interior.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
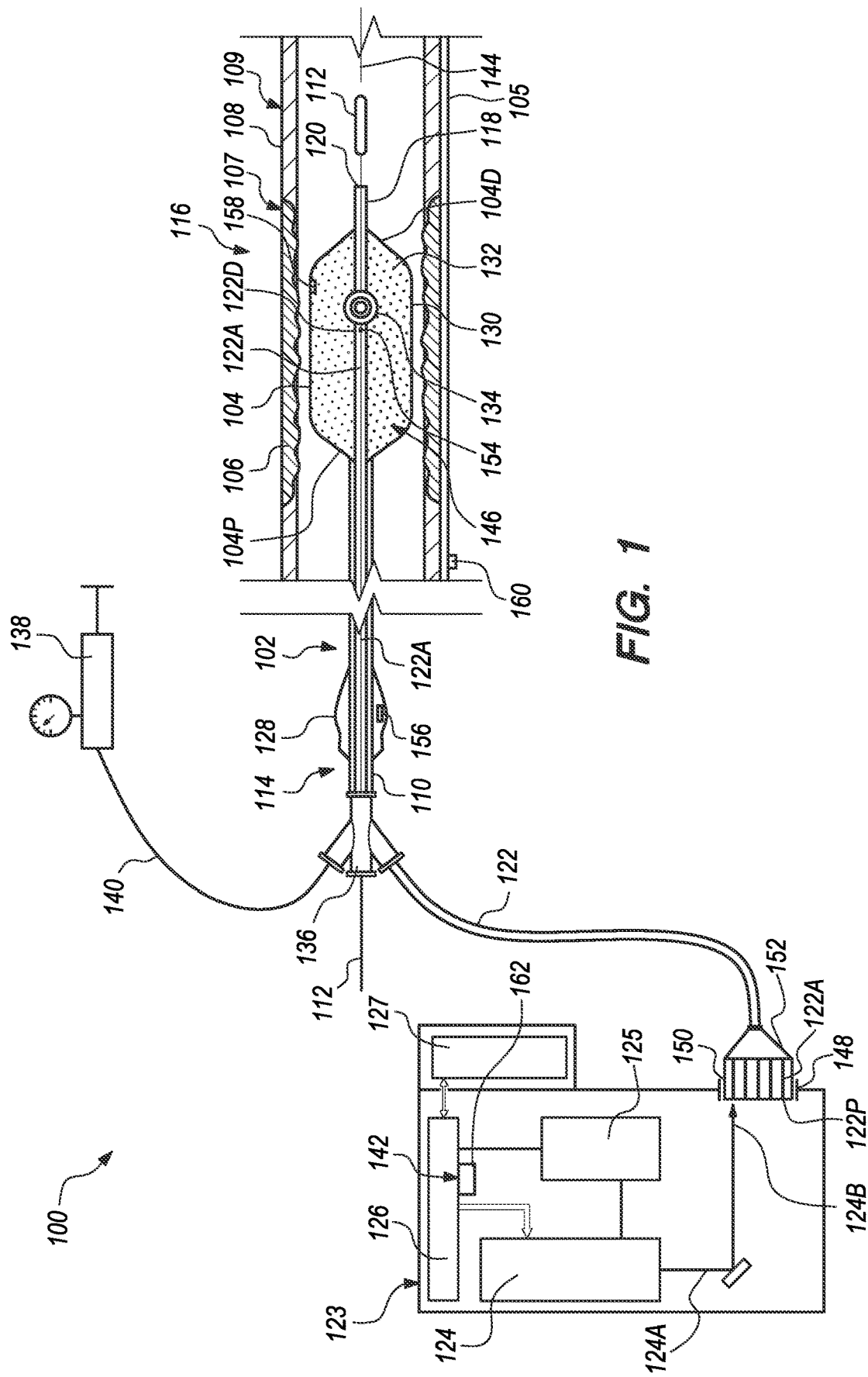
FIG. 1 is a schematic cross-sectional view of an embodiment of a catheter system in accordance with various embodiments herein, the catheter system including an electrical analyzer assembly having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

The catheter systems and related methods disclosed herein are configured to monitor the performance, reliability and safety of an intravascular lithotripsy catheter. In various embodiments, the catheter systems of the present invention utilize an energy source, e.g., a light source such as a laser source or another suitable energy source, which provides energy that is guided by an energy guide, e.g., a light guide, to create a localized plasma in a balloon fluid within a balloon interior of an inflatable balloon of the catheter. As such, the energy guide can sometimes be referred to as, or can be said to incorporate a "plasma generator" at or near a guide distal end of the energy guide that is positioned within the balloon interior. This localized plasma, in turn, induces a high energy bubble inside the balloon interior to create pressure waves to impart pressure onto and induce fractures in a treatment site, such as a calcified vascular lesion or a fibrous vascular lesion, at a treatment site within or adjacent to a blood vessel wall or a heart valve within a body of a patient.

In particular, in various embodiments, the catheter systems can include a catheter configured to advance to the treatment site within or adjacent a blood vessel or heart valve within the body of the patient. The catheter includes a catheter shaft, and a balloon that is coupled and/or secured to the catheter shaft. The balloons herein can include a balloon wall that defines the balloon interior and can be configured to receive the balloon fluid within the balloon interior to expand from a collapsed configuration suitable for advancing the catheter through a patient's vasculature, to an expanded configuration suitable for anchoring the catheter in position relative to the treatment site. The catheter systems also include one or more energy guides, e.g., light guides, disposed along the catheter shaft and within the balloon. Each energy guide can be configured for generating pressure waves within the balloon for disrupting the treatment sites. The catheter systems utilize energy from an energy source, e.g., light energy from a light source, to generate the plasma, i.e. via the plasma generator, within the balloon fluid at or near a guide distal end of the energy guide disposed in the balloon located at the treatment site. The plasma formation can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves within the balloon fluid retained within the balloon and thereby impart pressure waves upon the treatment site. In some embodiments, the energy source can be configured to provide sub-millisecond pulses of energy, e.g., light energy, from the energy source to initiate plasma formation in the balloon fluid within the balloon to cause rapid bubble formation and to impart pressure waves upon the balloon wall at the treatment site. Thus, the pressure waves can transfer mechanical energy through an incompressible balloon fluid to the treatment site to impart a fracture force on the vascular lesion.

As used herein, the terms "intravascular lesion", "vascular lesion" and "treatment site" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more vascular lesions within or adjacent a vessel wall of a blood vessel or a heart valve within a body of a patient. In the embodiment illustrated in FIG. 1, the catheter system 100 can include one or more of a catheter 102, a light guide bundle 122 including one or more light guides 122A, a source manifold 136, a fluid pump 138, a system console 123 including one or more of a light source 124, a power source 125, a system controller 126, and a graphic user interface 127 (a "GUI"), a handle assembly 128, and an electrical analyzer assembly 142.

The catheter 102 is configured to move to a treatment site 106 within or adjacent to a blood vessel 108 within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. The catheter shaft 110 can further include an inflation lumen (not shown). In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. In some embodiments, each light guide 122A can be an optical fiber and the light source 124 can be a laser. The light source 124 can be in optical communication with the light guides 122A at the proximal portion 114 of the catheter system 100.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, it is further appreciated that the light guides 122A described herein can be disposed uniformly or non-uniformly about the guidewire lumen 118 and/or the catheter shaft 110 to achieve the desired effect in the desired locations.

The balloon 104 can include a balloon wall 130 that defines a balloon interior 146, and can be inflated with a balloon fluid 132 to expand from a collapsed configuration suitable for advancing the catheter 102 through a patient's vasculature, to an expanded configuration suitable for anchoring the catheter 102 in position relative to the treatment site 106. Stated in another manner, when the balloon 104 is in the expanded configuration, the balloon wall 130 of the balloon 104 is configured to be positioned substantially adjacent to the treatment site 106. In some embodiments, the light source 124 of the catheter system 100 can be configured to provide sub-millisecond pulses of light from the light source 124, along the light guides 122A, to a location within the balloon interior 146 of the balloon 104, thereby inducing plasma formation in the balloon fluid 132 within the balloon interior 146 of the balloon 104. The plasma formation causes rapid bubble formation, and imparts pressure waves upon the treatment site 106. Exemplary plasma-induced bubbles are shown as bubbles 134 in FIG. 1.

It is appreciated that although the catheter systems 100 illustrated herein are generally described as including a light source 124 and one or more light guides 122A, the catheter system 100 can alternatively include any suitable energy source and energy guides for purposes of generating the desired plasma in the balloon fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, forms the pressure waves within the balloon fluid 132 that are utilized to provide the fracture force onto the treatment site 106. Still alternatively, the energy source 124 and/or the energy guides 122A can have another suitable design and/or configuration.

The balloons 104 suitable for use in the catheter systems 100 described in detail herein include those that can be passed through the vasculature of a patient when in the collapsed configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pa., USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 12 mm in diameter. In some embodiments, the balloons 104 can include those having diameters ranging from at least one mm to five mm in diameter.

Additionally, in some embodiments, the balloons 104 herein can include those having a length ranging from at least five mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations at the treatment site 106.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen light source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluids 132 can include those that include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 µm) lasers, or erbium:YAG (Er:YAG–emission maximum=2.94 µm) lasers. In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the light source 124. Various light sources 124 having emission wavelengths of at least ten nanometers to one millimeter are discussed elsewhere herein.

It is appreciated that the catheter system 100 and/or the light guide bundle 122 disclosed herein can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A herein can include an optical fiber or flexible light pipe. The light guides 122A herein can be thin and flexible and can allow light signals to be sent with very little loss of strength. The light guides 122A herein can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light along its length from a proximal portion, i.e. a guide proximal end 122P, to a distal portion, i.e. a guide distal end 122D, having at least one optical window (not shown) that is positioned within the balloon interior 146. The light guides 122A can create a light path as a portion of an optical network including the light source 124. The light path within the optical network allows light to travel from one part of the network to another. Both the optical fiber and the flexible light pipe can provide a light path within the optical networks herein.

Further, the light guides 122A herein can assume many configurations about and/or relative to the catheter shaft 110 of the catheters 102 described herein. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A herein can be disposed within one or more light guide lumens within the catheter shaft 110.

Additionally, it is further appreciated that the light guides 122A can be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118.

Further, the light guides 122A herein can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. It is appreciated that the direction of the acoustic wave can be tailored by changing an angle of the guide distal end 122D of the light guide 122A.

It is further appreciated that the photoacoustic transducers 154 disposed at the guide distal end 122D of the light guide 122A herein can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the light guide 122A can further include additional photoacoustic transducers 154 disposed along one or more side surfaces of the length of the light guide 122A.

The light guides 122A described herein can further include one or more diverting features or "diverters" (not shown in FIG. 1) within the light guide 122A that are configured to direct light to exit the light guide 122A toward a side surface e.g., at or near the guide distal end 122D of the light guide 122A, and toward the balloon wall 130. A diverting feature can include any feature of the system herein that diverts light from the light guide 122A away from its axial path toward a side surface of the light guide 122A. Additionally, the light guides 122A can each include one or more light windows disposed along the longitudinal or axial surfaces of each light guide 122A and in optical communication with a diverting feature. Stated in another manner, the diverting features herein can be configured to direct light in the light guide 122A toward a side surface, e.g., at or near the guide distal end 122D, where the side surface is in optical communication with a light window. The light windows can include a portion of the light guide 122A that allows light to exit the light guide 122A from within the light guide 122A, such as a portion of the light guide 122A lacking a cladding material on or about the light guide 122A.

Examples of the diverting features suitable for use herein include a reflecting element, a refracting element, and a fiber diffuser. Additionally, the diverting features suitable for focusing light away from the tip of the light guides 122A herein can include, but are not to be limited to, those having a convex surface, a gradient-index (GRIN) lens, and a mirror focus lens. Upon contact with the diverting feature, the light is diverted within the light guide 122A to the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the plurality of light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132, i.e. via the inflation conduit 140, as needed.

As noted above, in the embodiment illustrated in FIG. 1, the system console 123 includes one or more of the light source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, and the GUI 127 can be provided within the catheter system 100 without the specific need for the system console 123.

Further, as illustrated in FIG. 1, in certain embodiments, at least a portion of the electrical analyzer assembly 142 can also be positioned substantially within the system console 123. Alternatively, components of the electrical analyzer assembly 142 can be positioned in a different manner than what is specifically shown in FIG. 1.

Additionally, as shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the desired mechanical coupling between the light guide bundle 122 and the system console 123.

Further, the light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

As provided herein, the light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, e.g., a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122.

The light source 124 can have any suitable design. In certain embodiments, as noted above, the light source 124 can be configured to provide sub-millisecond pulses of light from the light source 124 that are focused onto a small spot in order to couple it into the guide proximal end 122P of the light guide 122A. Such pulses of light energy are then directed along the light guides 122A to a location within the balloon 104, thereby inducing plasma formation in the balloon fluid 132 within the balloon interior 146 of the balloon 104. In particular, the light energy emitted at the guide distal end 122D of the light guide 122A energizes the plasma generator to form the plasma within the balloon fluid 132 within the balloon interior 146. The plasma formation causes rapid bubble formation, and imparts pressure waves upon the treatment site 106. In such embodiments, the sub-millisecond pulses of light from the light source 124 can be delivered to the treatment site 106 at a frequency of between approximately one hertz (Hz) and 5000 Hz. In some embodiments, the sub-millisecond pulses of light from the light source 124 can be delivered to the treatment site 106 at a frequency of between approximately 30 Hz and 1000 Hz. In other embodiments, the sub-millisecond pulses of light from the light source 124 can be delivered to the treatment site 106 at a frequency of between approximately ten Hz and 100 Hz. In yet other embodiments, the sub-millisecond pulses of light from the light source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (μs) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 200 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the light sources 124 suitable for use in the catheter systems 100 herein can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the light guides 122A when the catheter 102 is placed at the treatment site 106. In some embodiments, the pressure waves can be imparted upon the treatment site 106 from a distance within a range from at least ten mm to 20 mm extending radially from the light guides 122A when the catheter 102 is placed at the treatment site 106. In other embodiments, the pressure waves can be imparted upon the treatment site 106 from a distance within a range from at least one mm to ten mm extending radially from the light guides 122A when the catheter 102 is placed at the treatment site 106. In yet other embodiments, the pressure waves can be imparted upon the treatment site 106 from a distance within a range from at least 1.5 mm to four mm extending radially from the light guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the light source 124, the system controller 126, the GUI 127, the handle assembly 128, and the electrical analyzer assembly 142. The power source 125 can have any suitable design for such purposes.

As noted, the system controller 126 is electrically coupled to and receives power from the power source 125. Additionally, the system controller 126 is coupled to and is configured to control operation of each of the light source 124, the GUI 127 and the electrical analyzer assembly 142. The system controller 126 can include one or more processors or circuits for purposes of controlling the operation of at least the light source 124, the GUI 127 and the electrical analyzer assembly 142. For example, the system controller 126 can control the light source 124 for generating pulses of light energy as desired, e.g., at any desired firing rate. Additionally, the system controller 126 can control and/or operate in conjunction with the electrical analyzer assembly 142 to effectively provide real-time continuous monitoring of the performance, reliability and safety of the catheter system 100.

Additionally, the system controller 126 can further be configured to control operation of other components of the catheter system 100, e.g., the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. Additionally, in this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, the GUI 127 and the electrical analyzer assembly 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. Additionally, in some embodiments, the circuitry 156 can receive electrical signals or data from the electrical analyzer assembly 142. Further, or in the alternative, the circuitry 156 can transmit such electrical signals or otherwise provide data to the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

As an overview, and as provided in greater detail herein, the electrical analyzer assembly 142 is configured to effectively monitor the performance, reliability and safety of the catheter system 100, in particular one that utilizes an energy source 124 to create a localized plasma which in turn induces a high energy bubble in the balloon fluid 132 within the balloon interior 146 of the balloon 104. More particularly, as described in detail herein, the electrical analyzer assembly 142 is specifically configured to effectively detect damage to, and/or rupturing or bursting of the balloon 104 during use of the catheter system 100.

During use of the catheter system 100, the generation of the localized plasma and the subsequent inducement of high energy bubbles in the balloon fluid 132 within the balloon interior 146 can cause the balloon fluid to heat up substantially, which, in addition to the pressure waves that are generated within the balloon interior 146, can put substantial stresses onto the balloon wall 130 of the balloon 104. Thus, the present invention is utilized to detect and/or identify when such stresses ultimately cause damage to the balloon 104, especially in the form of the potential rupturing or bursting of the balloon 104. As provided herein, if the electrical analyzer assembly 142 provides an indication, e.g., to the system controller 126, that the balloon 104 has ruptured, it is important and necessary that the procedure be stopped immediately, as such a failure presents a substantial risk to the patient 109, including potential harms such as tissue burns. Thus, with the invention described herein, the rupture of the balloon 104 can be quickly and successfully detected, and an indicator or signal can be provided that is used to lock out the energy source 124. This provides a necessary safety interlock for a potentially hazardous condition in which the balloon fluid 132 is able to leak out.

The design of the electrical analyzer assembly 142 can be varied to suit the specific requirements of the catheter system 100. In various embodiments, as described herein, the electrical analyzer assembly 142 can include one or more of a first electrode 158, a second electrode 160, and an impedance detector 162. Alternatively, the electrical analyzer assembly 142 can include more components or fewer components than what is specifically illustrated and described herein.

The first electrode 158 can be positioned at any suitable location within the catheter system 100 so that it is in communication with the balloon fluid 132 that is positioned within the balloon interior 146 of the balloon 104. For example, in some embodiments, as shown in FIG. 1, the first electrode 158 can be positioned within the balloon interior 146. Alternatively, the first electrode 158 can be positioned in another suitable location that is in communication with the balloon fluid 132 within the balloon interior 146. For example, in certain non-exclusive alternative embodiments, the first electrode 158 can be positioned within the handle assembly 128, within and/or adjacent to the inflation conduit 140, within and/or adjacent to the inflation lumen, and/or in another suitable location.

Additionally, the second electrode 160 can be positioned at any suitable location within the catheter system 100 so that it is in communication with the blood of the patient, i.e. so that no nonconductive materials of the catheter system 100 are positioned between the second electrode 160 and the blood of the patient 109. For example, in some embodiments, as shown in FIG. 1, the second electrode 160 can be positioned on and/or adjacent to the skin 105 of the patient 109. Alternatively, the second electrode 160 can be positioned in another suitable location that is in communication with the blood of the patient 109. For example, in certain non-exclusive alternative embodiments, the second electrode 160 can be positioned inside the fluid channel within the guidewire lumen 118, on the guidewire 112, and/or in another suitable location.

It is appreciated that with the general design of the electrical analyzer assembly 142 described herein, while the first electrode 158 is in communication with the balloon fluid 132 within the balloon interior 146, during normal operation the first electrode 158 is not in communication with the blood of the patient 109 as at least the nonconductive materials of the balloon 104 are positioned therebetween. Similarly, it is further appreciated that while the second electrode 160 is in communication with the blood of the patient 109, during normal operation the second electrode 160 is not in communication with the balloon fluid 132 within the balloon interior 146 as at least the nonconductive materials of the balloon 104 are positioned therebetween.

As noted above, the impedance detector 162 is connected in electrical communication with each of the first electrode 158 and the second electrode 160. As such, the impedance detector 162 is configured to detect and thus provide real-time continuous monitoring of the impedance between the first electrode 158 and the second electrode 160. Impedance is the effective measurement of the degree a body resists the flow of electrical current, with the body's fluid and tissues acting as conductors of electrical current. It is appreciated that the impedance detector 162 can be electrically coupled to each of the first electrode 158 and the second electrode 160 via a wireless connection, or via a wired connection.

The impedance detector 162 can be positioned in any suitable location where it can be in electrical communication with the first electrode 158 and the second electrode 160. For example, in some embodiments, as shown in FIG. 1, the impedance detector 162 can be positioned substantially within the system console 123 and/or adjacent to the system controller 126. Alternatively, the impedance detector 162 can be positioned in another suitable location within the catheter system 100. For example, in certain non-exclusive alternative embodiments, the impedance detector 162 can be positioned within and/or adjacent to the handle assembly 128, inside the catheter 102, and/or in another suitable location.

As provided herein, the impedance detector 162 is configured to detect the impedance between the first electrode 158 and the second electrode 160 during operation of the catheter system 100. The impedance detector 162 can then generate a detector signal or detector output, e.g., electrical signals regarding the detected impedance, and send the detector signal or detector output to the system controller 126 and/or the circuitry 156 within the handle assembly 128 for processing. The system controller 126 can then provide appropriate information to the user or operator, e.g., via the GUI 127, as to the status of operation of the catheter system 100, e.g., the potential rupturing of the balloon 104. It is appreciated that the impedance detector 162 can be electrically connected to the system controller 126 via a wireless connection, or via a wired connection.

Under normal operating circumstances, the detected impedance would be very high, e.g., within an expected impedance range, since the first electrode 158 is insulated from the second electrode 160 by the nonconductive materials of the catheter 102. Additionally, the impedance detector 162 and/or the system controller 126 would process the detector signal to look for sudden drops in impedance between the electrodes 158, 160, which would indicate a rupture of the balloon 104, since a ruptured balloon 104 would remove the insulated barrier between the electrodes 158, 160.

Thus, in summary, if the balloon 104 ruptures, the procedure must be stopped immediately. The present invention detects this failure and provides an indicator or signal that the system controller 126 could use to lock out the energy source 124. This provides a necessary safety interlock for a potentially hazardous condition in which the energy source 124 is able to leak out of the ruptured balloon 104. Moreover, the signal could be used to indicate to the user or operator, e.g., via the GUI 127, to halt the procedure and remove the balloon 104 from the patient 109 under treatment.

Figure 2:
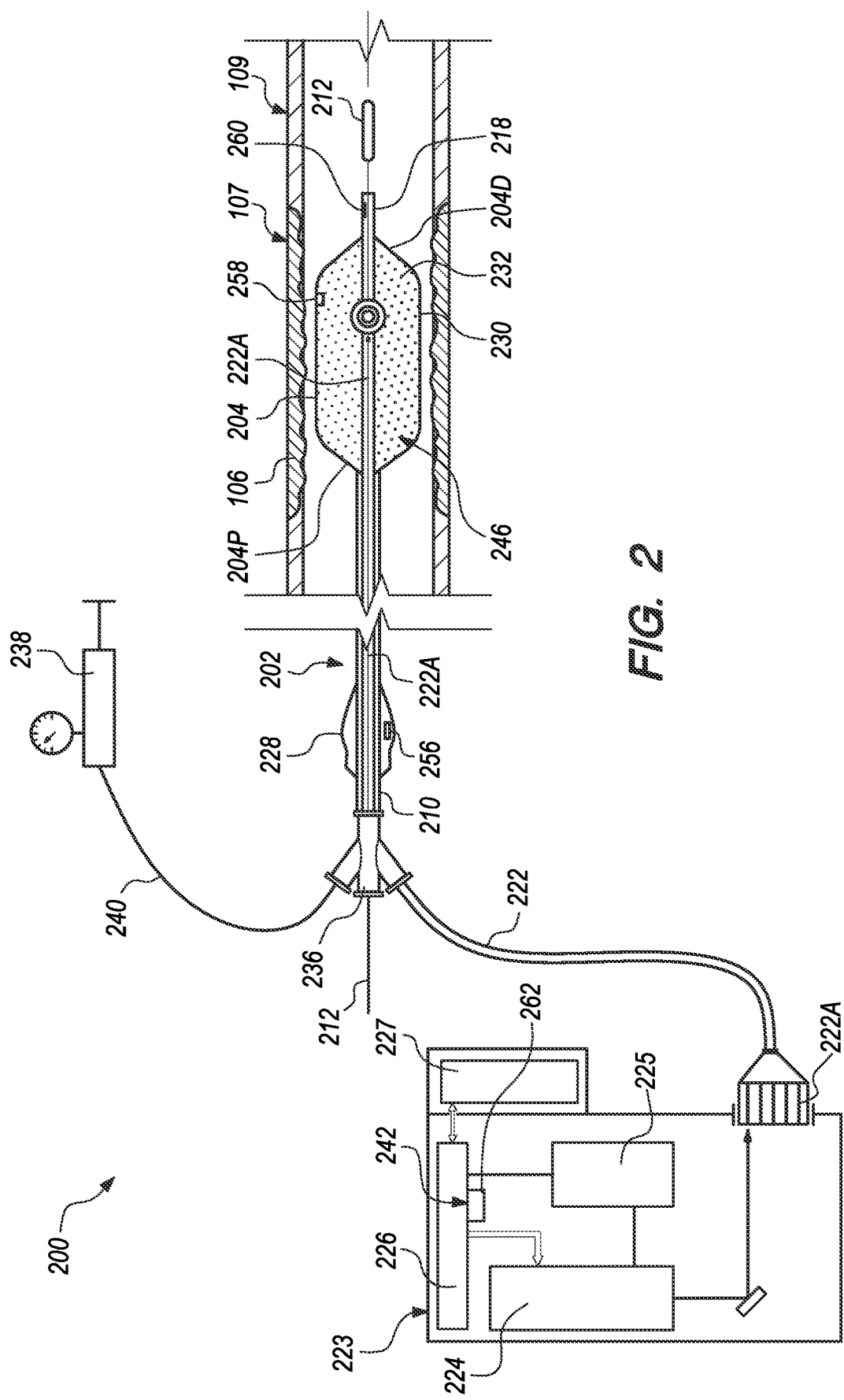
FIG. 2 is a schematic cross-sectional view of another embodiment of the catheter system including another embodiment of the electrical analyzer assembly.

FIG. 2 is a schematic cross-sectional view of another embodiment of the catheter system 200 including another embodiment of the electrical analyzer assembly 242. The design of the catheter system 200 is substantially similar to the embodiment illustrated and described herein above. In particular, in the embodiment shown in FIG. 2, the catheter system 200 can again include a catheter 202 including a catheter shaft 210, a balloon 204 having a balloon wall 230 that defines a balloon interior 246, a balloon proximal end 204P, and a balloon distal end 204D, a balloon fluid 232 that is retained substantially within the balloon interior 246, a guidewire 212, and a guidewire lumen 218 that extends into the balloon interior 246; an energy guide bundle 222 including one or more energy guides 222A; a source manifold 236; a fluid pump 238; a system console 223 including one or more of an energy source 224, a power source 225, a system controller 226, and a GUI 227; a handle assembly 228; and the electrical analyzer assembly 242. Alternatively, in other embodiments, the catheter system 200 can include more components or fewer components than what is specifically illustrated and described herein.

The catheter 202, including the catheter shaft 210, the balloon 204, the guidewire 212, and the guidewire lumen 218, is generally similar in design and operation to what has been described in detail herein above. Thus, such components will not be described in detail again in relation to the embodiment shown in FIG. 2.

As above, the balloon 204 is selectively movable between a collapsed configuration suitable for advancing the catheter 202 through a patient's vasculature, and an expanded configuration suitable for anchoring the catheter 202 in position relative to the treatment site 106. In some embodiments, the balloon proximal end 204P can be coupled to the catheter shaft 210, and the balloon distal end 204D can be coupled to the guidewire lumen 218. Additionally, the balloon 204 can be inflated with the balloon fluid 232, e.g., from the fluid pump 238, that is directed into the balloon interior 246 of the balloon 204 via the inflation conduit 240.

Additionally, the energy guide bundle 222 including the one or more energy guides 222A, and the system console 223 including one or more of the energy source 224, the power source 225, the system controller 226, and the GUI 227, are generally similar in design and operation to what has been described in detail herein above. Accordingly, such components will not be described in detail again in relation to the embodiment shown in FIG. 2.

Further, as above, the handle assembly 228 is handled and used by the user or operator to operate, position and control the catheter 202. Additionally, as shown in the embodiment illustrated in FIG. 2, the handle assembly 228 can again include circuitry 256 that can form a portion of the system controller 226. Alternatively, the handle assembly 228 can be configured without the circuitry 256.

As with the previous embodiment, the electrical analyzer assembly 242 is again configured to monitor the performance, reliability and safety of the catheter system 200. Additionally, the design of the electrical analyzer assembly 242 can be somewhat similar to what was illustrated and described herein above in relation to the embodiment shown in FIG. 1. For example, the electrical analyzer assembly 242 can again include a first electrode 258, a second electrode 260, and an impedance detector 262 that is connected in electrical communication with the first electrode 258 and the second electrode 260 in order to effectively measure and/or detect the impedance between the first electrode 258 and the second electrode 260.

However, in the embodiment shown in FIG. 2, one or more of the first electrode 258, the second electrode 260 and the impedance detector 262 can be positioned in a different manner than in the previous embodiment. More particularly, as shown in FIG. 2, in this embodiment, the first electrode 258 is again positioned within the balloon interior 246, and the impedance detector 262 is again positioned adjacent to and/or in electrical communication with the system controller 226, but the second electrode 260 is now positioned inside the fluid channel within the guidewire lumen 218.

It is appreciated that with such design, during normal operation, the first electrode 258 is still in communication with the balloon fluid 232 within the balloon interior 246, but not in communication with the blood of the patient 109; and the second electrode 260 is still in communication with the blood of the patient 109, but not in communication with the balloon fluid 232 within the balloon interior 246. Additionally, it is further appreciated that with such design, the impedance detector 262, in conjunction with the system controller 226 and/or the circuitry 256 in the handle assembly 228, is still configured to look for sudden drops in impedance between the electrodes 258, 260 as an indication of damage to and/or rupture of the balloon 204, which would necessitate that the procedure be immediately stopped and the catheter 202 removed from the patient 109.

Figure 3:
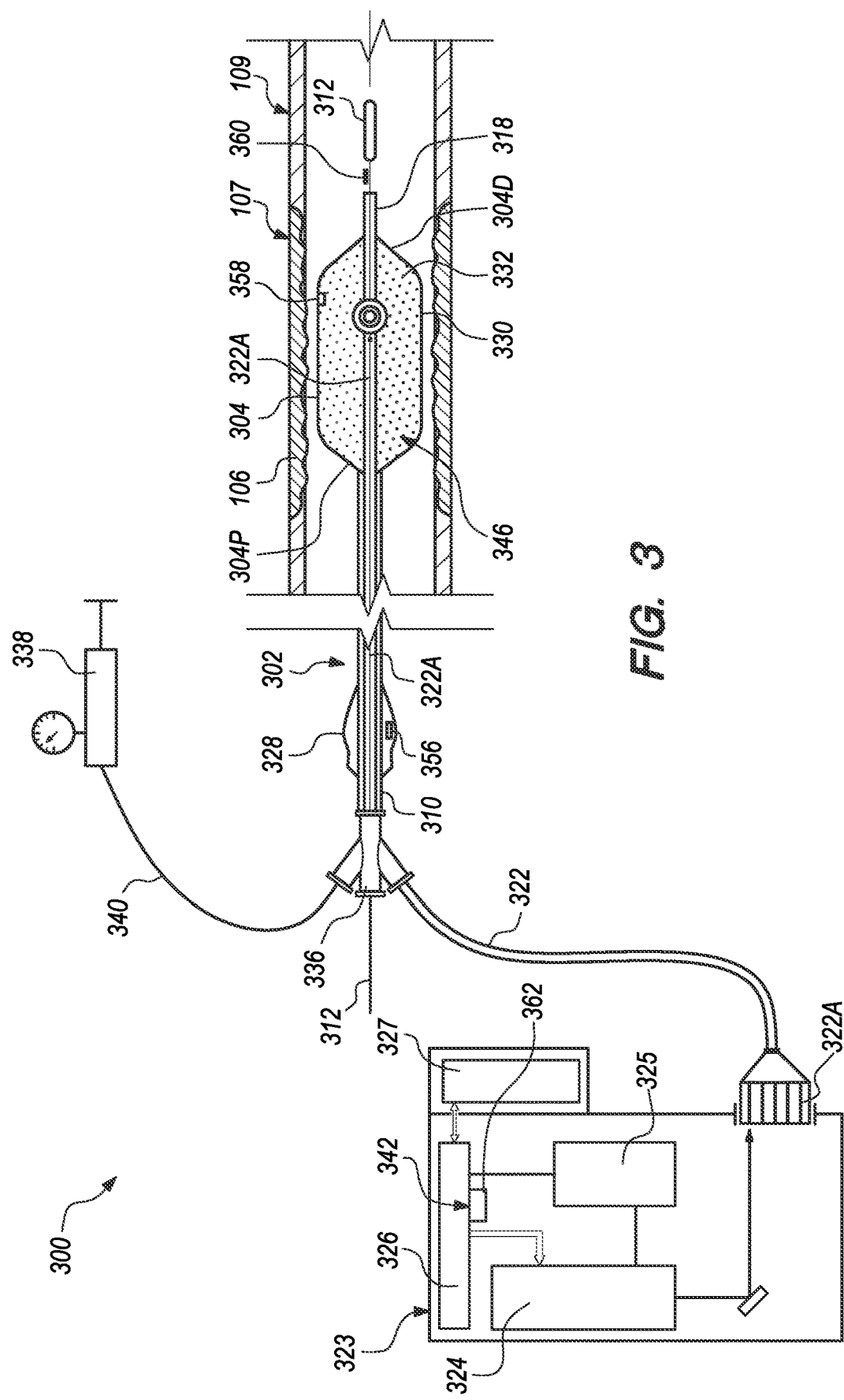
FIG. 3 is a schematic cross-sectional view of still another embodiment of the catheter system including still another embodiment of the electrical analyzer assembly.

FIG. 3 is a schematic cross-sectional view of still another embodiment of the catheter system 300 including still another embodiment of the electrical analyzer assembly 342. The design of the catheter system 300 is substantially similar to the embodiments illustrated and described herein above. In particular, in the embodiment shown in FIG. 3, the catheter system 300 can again include a catheter 302 including a catheter shaft 310, a balloon 304 having a balloon wall 330 that defines a balloon interior 346, a balloon proximal end 304P, and a balloon distal end 304D, a balloon fluid 332 that is retained substantially within the balloon interior 346, a guidewire 312, and a guidewire lumen 318 that extends into the balloon interior 346; an energy guide bundle 322 including one or more energy guides 322A; a source manifold 336; a fluid pump 338; a system console 323 including one or more of an energy source 324, a power source 325, a system controller 326, and a GUI 327; a handle assembly 328; and the electrical analyzer assembly 342. Alternatively, in other embodiments, the catheter system 300 can include more components or fewer components than what is specifically illustrated and described herein.

The catheter 302, including the catheter shaft 310, the balloon 304, the guidewire 312, and the guidewire lumen 318, is generally similar in design and operation to what has been described in detail herein above. Thus, such components will not be described in detail again in relation to the embodiment shown in FIG. 3.

As above, the balloon 304 is selectively movable between a collapsed configuration suitable for advancing the catheter 302 through a patient's vasculature, and an expanded configuration suitable for anchoring the catheter 302 in position relative to the treatment site 106. In some embodiments, the balloon proximal end 304P can be coupled to the catheter shaft 310, and the balloon distal end 304D can be coupled to the guidewire lumen 318. Additionally, the balloon 304 can be inflated with the balloon fluid 332, e.g., from the fluid pump 338, that is directed into the balloon interior 346 of the balloon 304 via the inflation conduit 340.

Additionally, the energy guide bundle 322 including the one or more energy guides 322A, and the system console 323 including one or more of the energy source 324, the power source 325, the system controller 326, and the GUI 327, are generally similar in design and operation to what has been described in detail herein above. Accordingly, such components will not be described in detail again in relation to the embodiment shown in FIG. 3.

Further, as above, the handle assembly 328 is handled and used by the user or operator to operate, position and control the catheter 302. Additionally, as shown in the embodiment illustrated in FIG. 3, the handle assembly 328 can again include circuitry 356 that can form a portion of the system controller 326. Alternatively, the handle assembly 328 can be configured without the circuitry 356.

As with the previous embodiments, the electrical analyzer assembly 342 is again configured to monitor the performance, reliability and safety of the catheter system 300. Additionally, the design of the electrical analyzer assembly 342 can be somewhat similar to what was illustrated and described herein above in relation to the previous embodiments. For example, the electrical analyzer assembly 342 can again include a first electrode 358, a second electrode 360, and an impedance detector 362 that is connected in electrical communication with the first electrode 358 and the second electrode 360 in order to effectively measure and/or detect the impedance between the first electrode 358 and the second electrode 360.

However, in the embodiment shown in FIG. 3, one or more of the first electrode 358, the second electrode 360 and the impedance detector 362 can be positioned in a different manner than in the previous embodiments. More particularly, as shown in FIG. 3, in this embodiment, the first electrode 358 is again positioned within the balloon interior 346, and the impedance detector 362 is again positioned adjacent to and/or in electrical communication with the system controller 326, but the second electrode 360 is now positioned on and/or adjacent to the guidewire 312.

It is appreciated that with such design, during normal operation, the first electrode 358 is still in communication with the balloon fluid 332 within the balloon interior 346, but not in communication with the blood of the patient 109; and the second electrode 360 is still in communication with the blood of the patient 109, but not in communication with the balloon fluid 332 within the balloon interior 346. Additionally, it is further appreciated that with such design, the impedance detector 362, in conjunction with the system controller 326 and/or the circuitry 356 in the handle assembly 328, is still configured to look for sudden drops in impedance between the electrodes 358, 360 as an indication of damage to and/or rupture of the balloon 304, which would necessitate that the procedure be immediately stopped and the catheter 302 be removed from the patient 109.

Figure 4:
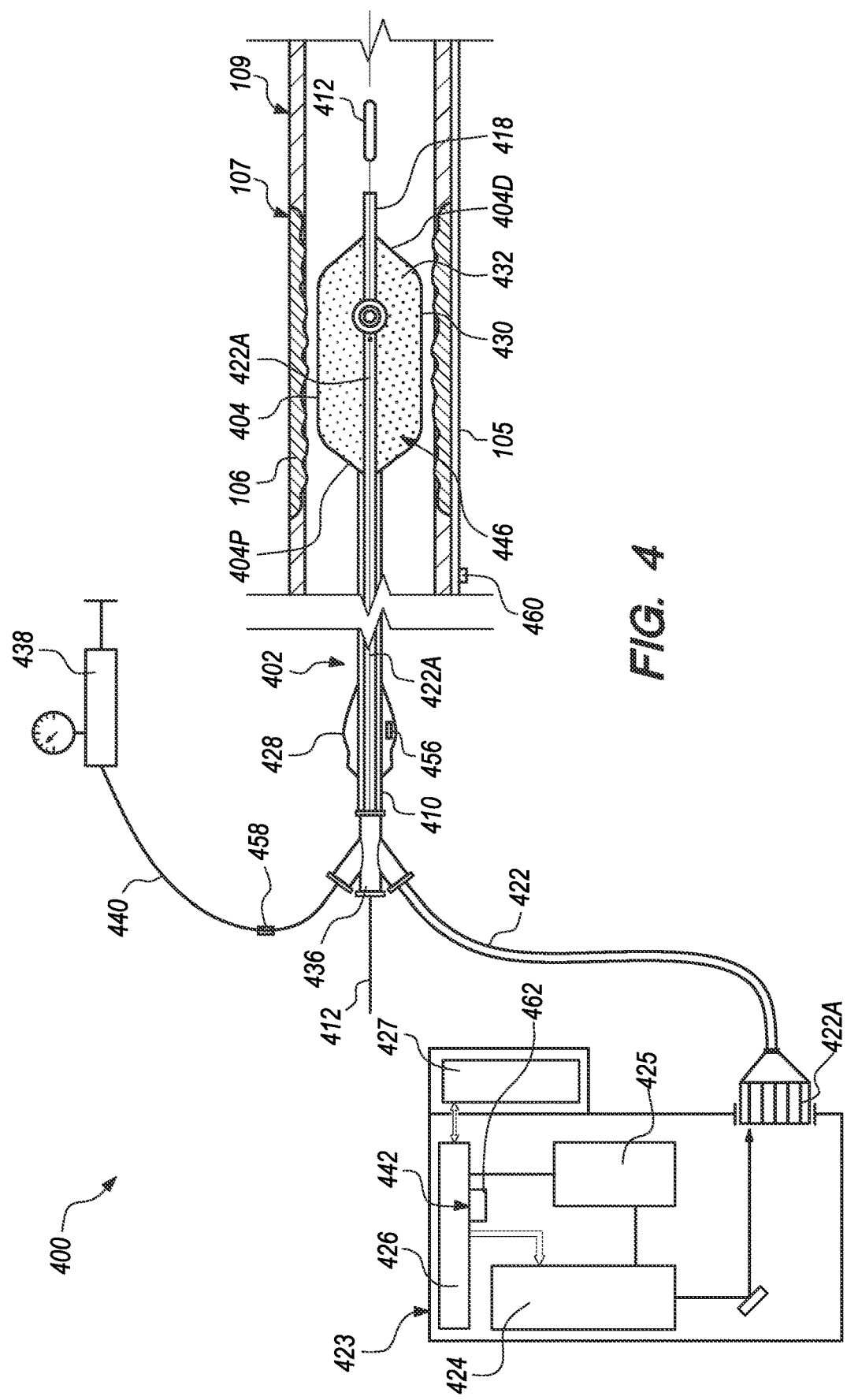
FIG. 4 is a schematic cross-sectional view of another embodiment of the catheter system including another embodiment of the electrical analyzer assembly.

FIG. 4 is a schematic cross-sectional view of another embodiment of the catheter system 400 including another embodiment of the electrical analyzer assembly 442. The design of the catheter system 400 is substantially similar to the embodiments illustrated and described herein above. In particular, in the embodiment shown in FIG. 4, the catheter system 400 can again include a catheter 402 including a catheter shaft 410, a balloon 404 having a balloon wall 430 that defines a balloon interior 446, a balloon proximal end 404P, and a balloon distal end 404D, a balloon fluid 432 that is retained substantially within the balloon interior 446, a guidewire 412, and a guidewire lumen 418 that extends into the balloon interior 446; an energy guide bundle 422 including one or more energy guides 422A; a source manifold 436; a fluid pump 438; a system console 423 including one or more of an energy source 424, a power source 425, a system controller 426, and a GUI 427; a handle assembly 428; and the electrical analyzer assembly 442. Alternatively, in other embodiments, the catheter system 400 can include more components or fewer components than what is specifically illustrated and described herein.

The catheter 402, including the catheter shaft 410, the balloon 404, the guidewire 412, and the guidewire lumen 418, is generally similar in design and operation to what has been described in detail herein above. Thus, such components will not be described in detail again in relation to the embodiment shown in FIG. 4.

As above, the balloon 404 is selectively movable between a collapsed configuration suitable for advancing the catheter 402 through a patient's vasculature, and an expanded configuration suitable for anchoring the catheter 402 in position relative to the treatment site 106. In some embodiments, the balloon proximal end 404P can be coupled to the catheter shaft 410, and the balloon distal end 404D can be coupled to the guidewire lumen 418. Additionally, the balloon 404 can be inflated with the balloon fluid 432, e.g., from the fluid pump 438, that is directed into the balloon interior 446 of the balloon 404 via the inflation conduit 440.

Additionally, the energy guide bundle 422 including the one or more energy guides 422A, and the system console 423 including one or more of the energy source 424, the power source 425, the system controller 426, and the GUI 427, are generally similar in design and operation to what has been described in detail herein above. Accordingly, such components will not be described in detail again in relation to the embodiment shown in FIG. 4.

Further, as above, the handle assembly 428 is handled and used by the user or operator to operate, position and control the catheter 402. Additionally, as shown in the embodiment illustrated in FIG. 4, the handle assembly 428 can again include circuitry 456 that can form a portion of the system controller 426. Alternatively, the handle assembly 428 can be configured without the circuitry 456.

As with the previous embodiments, the electrical analyzer assembly 442 is again configured to monitor the performance, reliability and safety of the catheter system 400. Additionally, the design of the electrical analyzer assembly 442 can be somewhat similar to what was illustrated and described herein above in relation to the previous embodiments. For example, the electrical analyzer assembly 442 can again include a first electrode 458, a second electrode 460, and an impedance detector 462 that is connected in electrical communication with the first electrode 458 and the second electrode 460 in order to effectively measure and/or detect the impedance between the first electrode 458 and the second electrode 460.

However, in the embodiment shown in FIG. 4, one or more of the first electrode 458, the second electrode 460 and the impedance detector 462 can be positioned in a different manner than in the previous embodiments. More particularly, as shown in FIG. 4, in this embodiment, the second electrode 460 is again positioned on and/or adjacent to the skin 105 of the patient 109 (as in the embodiment shown in FIG. 1), and the impedance detector 462 is again positioned adjacent to and/or in electrical communication with the system controller 426, but the first electrode 458 is now positioned within and/or adjacent to the inflation conduit 440 through which balloon fluid 432 is directed into the balloon interior 446 of the balloon 404.

It is appreciated that with such design, during normal operation, the first electrode 458 is still in communication with the balloon fluid 432 within the balloon interior 446, but not in communication with the blood of the patient 109; and the second electrode 460 is still in communication with the blood of the patient 109, but not in communication with the balloon fluid 432 within the balloon interior 446. Additionally, it is further appreciated that with such design, the impedance detector 462, in conjunction with the system controller 426 and/or the circuitry 456 in the handle assembly 428, is still configured to look for sudden drops in impedance between the electrodes 458, 460 as an indication of damage to and/or rupture of the balloon 404, which would necessitate that the procedure be immediately stopped and the catheter 402 be removed from the patient 109.

Figure 5:
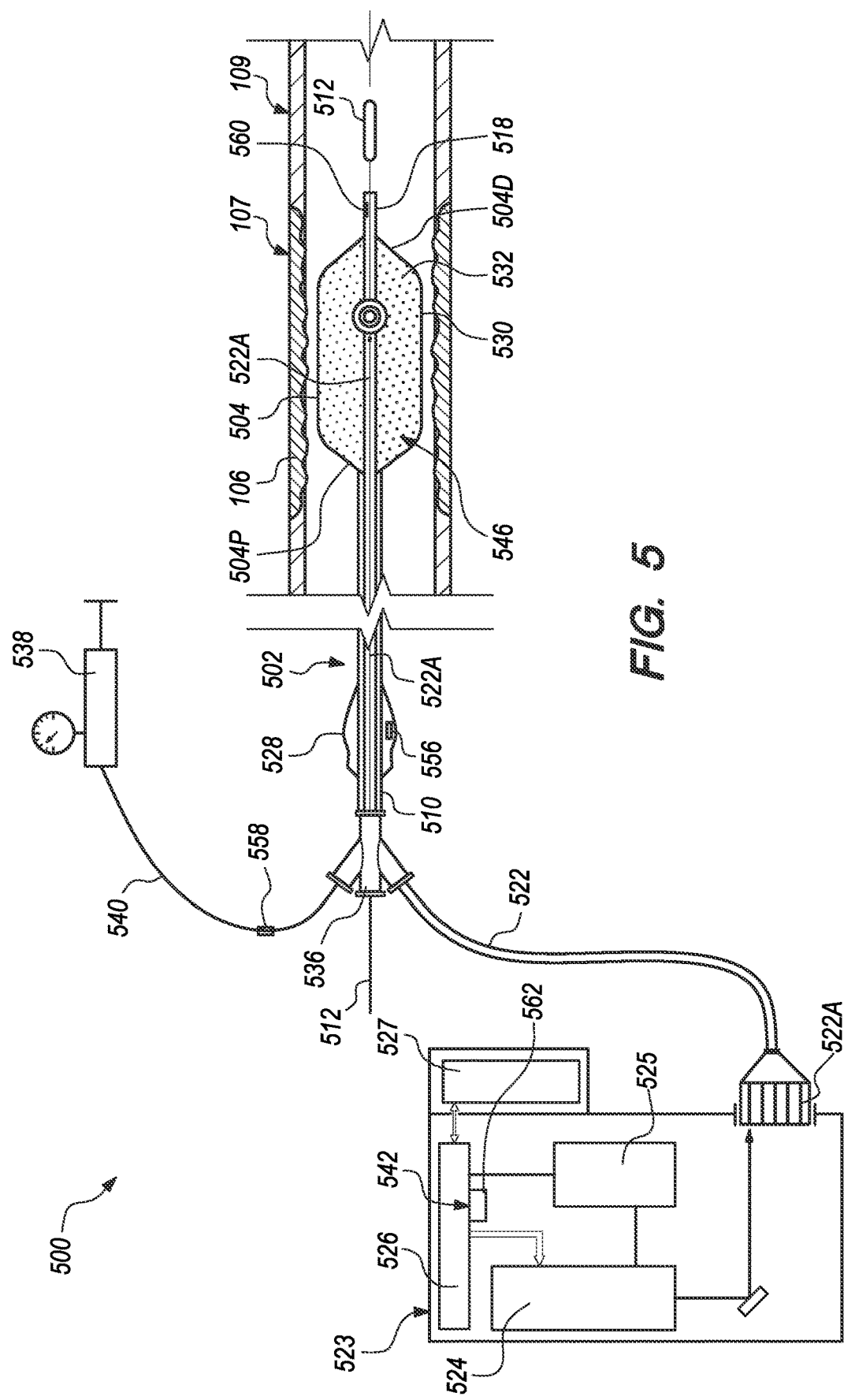
FIG. 5 is a schematic cross-sectional view of yet another embodiment of the catheter system including yet another embodiment of the electrical analyzer assembly.

FIG. 5 is a schematic cross-sectional view of yet another embodiment of the catheter system 500 including yet another embodiment of the electrical analyzer assembly 542. The design of the catheter system 500 is substantially similar to the embodiments illustrated and described herein above. In particular, in the embodiment shown in FIG. 5, the catheter system 500 can again include a catheter 502 including a catheter shaft 510, a balloon 504 having a balloon wall 530 that defines a balloon interior 546, a balloon proximal end 504P, and a balloon distal end 504D, a balloon fluid 532 that is retained substantially within the balloon interior 546, a guidewire 512, and a guidewire lumen 518 that extends into the balloon interior 546; an energy guide bundle 522 including one or more energy guides 522A; a source manifold 536; a fluid pump 538; a system console 523 including one or more of an energy source 524, a power source 525, a system controller 526, and a GUI 527; a handle assembly 528; and the electrical analyzer assembly 542. Alternatively, in other embodiments, the catheter system 500 can include more components or fewer components than what is specifically illustrated and described herein.

The catheter 502, including the catheter shaft 510, the balloon 504, the guidewire 512, and the guidewire lumen 518, is generally similar in design and operation to what has been described in detail herein above. Thus, such components will not be described in detail again in relation to the embodiment shown in FIG. 5.

As above, the balloon 504 is selectively movable between a collapsed configuration suitable for advancing the catheter 502 through a patient's vasculature, and an expanded configuration suitable for anchoring the catheter 502 in position relative to the treatment site 106. In some embodiments, the balloon proximal end 504P can be coupled to the catheter shaft 510, and the balloon distal end 504D can be coupled to the guidewire lumen 518. Additionally, the balloon 504 can be inflated with the balloon fluid 532, e.g., from the fluid pump 538, that is directed into the balloon interior 546 of the balloon 504 via the inflation conduit 540.

Additionally, the energy guide bundle 522 including the one or more energy guides 522A, and the system console 523 including one or more of the energy source 524, the power source 525, the system controller 526, and the GUI 527, are generally similar in design and operation to what has been described in detail herein above. Accordingly, such components will not be described in detail again in relation to the embodiment shown in FIG. 5.

Further, as above, the handle assembly 528 is handled and used by the user or operator to operate, position and control the catheter 502. Additionally, as shown in the embodiment illustrated in FIG. 5, the handle assembly 528 can again include circuitry 556 that can form a portion of the system controller 526. Alternatively, the handle assembly 528 can be configured without the circuitry 556.

As with the previous embodiments, the electrical analyzer assembly 542 is again configured to monitor the performance, reliability and safety of the catheter system 500. Additionally, the design of the electrical analyzer assembly 542 can be somewhat similar to what was illustrated and described herein above in relation to the previous embodiments. For example, the electrical analyzer assembly 542 can again include a first electrode 558, a second electrode 560, and an impedance detector 562 that is connected in electrical communication with the first electrode 558 and the second electrode 560 in order to effectively measure and/or detect the impedance between the first electrode 558 and the second electrode 560.

However, in the embodiment shown in FIG. 5, one or more of the first electrode 558, the second electrode 560 and the impedance detector 562 can be positioned in a different manner than in the previous embodiments. More particularly, as shown in FIG. 5, in this embodiment, the first electrode 558 is again positioned within and/or adjacent to the inflation conduit 540 through which balloon fluid 532 is directed into the balloon interior 546 of the balloon 504 (as in FIG. 4), the second electrode 560 is again positioned within and/or adjacent to the guidewire lumen 518 (as in the embodiment shown in FIG. 2), and the impedance detector 562 is again positioned adjacent to and/or in electrical communication with the system controller 526.

It is appreciated that with such design, during normal operation, the first electrode 558 is still in communication with the balloon fluid 532 within the balloon interior 546, but not in communication with the blood of the patient 109; and the second electrode 560 is still in communication with the blood of the patient 109, but not in communication with the balloon fluid 532 within the balloon interior 546. Additionally, it is further appreciated that with such design, the impedance detector 562, in conjunction with the system controller 526 and/or the circuitry 556 in the handle assembly 528, is still configured to look for sudden drops in impedance between the electrodes 558, 560 as an indication of damage to and/or rupture of the balloon 504, which would necessitate that the procedure be immediately stopped and the catheter 502 be removed from the patient 109.

Figure 6:
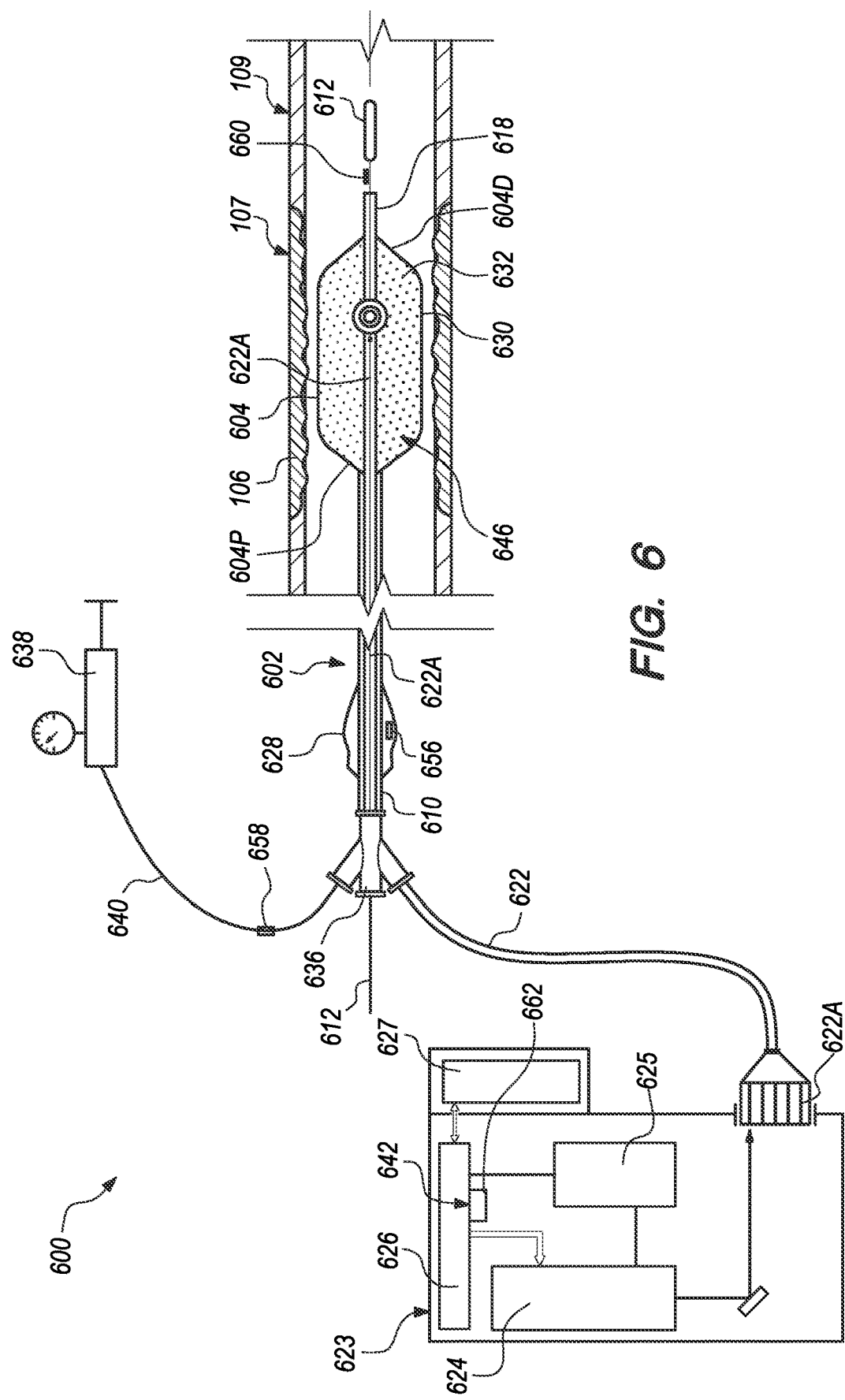
FIG. 6 is a schematic cross-sectional view of still yet another embodiment of the catheter system including still yet another embodiment of the electrical analyzer assembly.

FIG. 6 is a schematic cross-sectional view of still yet another embodiment of the catheter system 600 including still yet another embodiment of the electrical analyzer assembly 642. The design of the catheter system 600 is substantially similar to the embodiments illustrated and described herein above. In particular, in the embodiment shown in FIG. 6, the catheter system 600 can again include a catheter 602 including a catheter shaft 610, a balloon 604 having a balloon wall 630 that defines a balloon interior 646, a balloon proximal end 604P, and a balloon distal end 604D, a balloon fluid 632 that is retained substantially within the balloon interior 646, a guidewire 612, and a guidewire lumen 618 that extends into the balloon interior 646; an energy guide bundle 622 including one or more energy guides 622A; a source manifold 636; a fluid pump 638; a system console 623 including one or more of an energy source 624, a power source 625, a system controller 626, and a GUI 627; a handle assembly 628; and the electrical analyzer assembly 642. Alternatively, in other embodiments, the catheter system 600 can include more components or fewer components than what is specifically illustrated and described herein.

The catheter 602, including the catheter shaft 610, the balloon 604, the guidewire 612, and the guidewire lumen 618, is generally similar in design and operation to what has been described in detail herein above. Thus, such components will not be described in detail again in relation to the embodiment shown in FIG. 6.

As above, the balloon 604 is selectively movable between a collapsed configuration suitable for advancing the catheter 602 through a patient's vasculature, and an expanded configuration suitable for anchoring the catheter 602 in position relative to the treatment site 106. In some embodiments, the balloon proximal end 604P can be coupled to the catheter shaft 610, and the balloon distal end 604D can be coupled to the guidewire lumen 618. Additionally, the balloon 604 can be inflated with the balloon fluid 632, e.g., from the fluid pump 638, that is directed into the balloon interior 646 of the balloon 604 via the inflation conduit 640.

Additionally, the energy guide bundle 622 including the one or more energy guides 622A, and the system console 623 including one or more of the energy source 624, the power source 625, the system controller 626, and the GUI 627, are generally similar in design and operation to what has been described in detail herein above. Accordingly, such components will not be described in detail again in relation to the embodiment shown in FIG. 6.

Further, as above, the handle assembly 628 is handled and used by the user or operator to operate, position and control the catheter 602. Additionally, as shown in the embodiment illustrated in FIG. 6, the handle assembly 628 can again include circuitry 656 that can form a portion of the system controller 626. Alternatively, the handle assembly 628 can be configured without the circuitry 656.

As with the previous embodiments, the electrical analyzer assembly 642 is again configured to monitor the performance, reliability and safety of the catheter system 600. Additionally, the design of the electrical analyzer assembly 642 can be somewhat similar to what was illustrated and described herein above in relation to the previous embodiments. For example, the electrical analyzer assembly 642 can again include a first electrode 658, a second electrode 660, and an impedance detector 662 that is connected in electrical communication with the first electrode 658 and the second electrode 660 in order to effectively measure and/or detect the impedance between the first electrode 658 and the second electrode 660.

However, in the embodiment shown in FIG. 6, one or more of the first electrode 658, the second electrode 660 and the impedance detector 662 can be positioned in a different manner than in the previous embodiments. More particularly, as shown in FIG. 6, in this embodiment, the first electrode 658 is again positioned within and/or adjacent to the inflation conduit 640 through which balloon fluid 632 is directed into the balloon interior 646 of the balloon 604 (as in FIG. 4), the second electrode 660 is again positioned on and/or adjacent to the guidewire 612 (as in the embodiment shown in FIG. 3), and the impedance detector 662 is again positioned adjacent to and/or in electrical communication with the system controller 626.

It is appreciated that with such design, during normal operation, the first electrode 658 is still in communication with the balloon fluid 632 within the balloon interior 646, but not in communication with the blood of the patient 109; and the second electrode 660 is still in communication with the blood of the patient 109, but not in communication with the balloon fluid 632 within the balloon interior 646. Additionally, it is further appreciated that with such design, the impedance detector 662, in conjunction with the system controller 626 and/or the circuitry 656 in the handle assembly 628, is still configured to look for sudden drops in impedance between the electrodes 658, 660 as an indication of damage to and/or rupture of the balloon 604, which would necessitate that the procedure be immediately stopped and the catheter 602 be removed from the patient 109.

As noted above, the electrical analyzer assembly of the present invention addresses several important challenges with the performance, reliability and safety of an intravascular lithotripsy catheter, in particular one that utilizes an energy source, e.g., a light source such as a laser source, to create a localized plasma which in turn induces a high energy bubble in the balloon fluid within the balloon interior of the balloon. For example, as noted above, issues that are addressed by the present invention include, but are not limited to: 1) electrical detection of normal operation and/or balloon condition used within the catheter system, and 2) electrical detection of a failure of the balloon, e.g., damage to and/or rupture of the balloon, during use of the catheter system, which would necessitate shutting down of the catheter system and removal of the catheter from the body of the patient.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall or heart valve within a body of a patient, the catheter system comprising:
   an energy source that generates energy;
   a balloon that is positionable substantially adjacent to the treatment site, the balloon having a balloon wall that defines a balloon interior, the balloon interior being configured to receive a balloon fluid;
   an energy guide that is configured to receive energy from the energy source and guide the energy into the balloon interior; and
   an electrical analyzer assembly that is configured to monitor a condition of the balloon during use of the catheter system, the electrical analyzer assembly including (i) a first electrode, (ii) a second electrode that is in fluid communication with blood of the patient, and (iii) an impedance detector, the impedance detector being electrically coupled to the first electrode and the second electrode, the impedance detector being configured to detect an impedance between the first electrode and the second electrode.

2. The catheter system of claim 1 wherein the electrical analyzer assembly analyzes an electrical signal and determines the condition of the balloon based at least in part on the electrical signal.

3. The catheter system of claim 2 wherein the electrical analyzer assembly analyzes the electrical signal and determines whether a rupture of the balloon has occurred based at least in part on the electrical signal.

4. The catheter system of claim 1 wherein when a rupture in the balloon has not occurred, the first electrode is in fluid communication with the balloon fluid in the balloon interior, and the second electrode is not in fluid communication with the balloon fluid in the balloon interior.

5. The catheter system of claim 1 wherein the impedance detector generates a detector signal based at least in part on the detected impedance between the first electrode and the second electrode.

6. The catheter system of claim 5 further comprising a system controller that is electrically coupled to the impedance detector, the system controller being configured to receive the detector signal from the impedance detector and determine the condition of the balloon based at least in part on the detector signal.

7. The catheter system of claim 6 wherein the impedance detector is electrically coupled to the system controller via a wired connection.

8. The catheter system of claim 6 wherein the impedance detector is electrically coupled to the system controller via a wireless connection.

9. The catheter system of claim 6 wherein the system controller is configured to recognize a normal condition of the balloon based at least in part on the detector signal.

10. The catheter system of claim 6 wherein the system controller is configured to recognize a potential rupture of the balloon based at least in part on the detector signal.

11. The catheter system of claim 10 wherein the system controller is configured to automatically shut down operation of the catheter system upon recognition of the potential rupture of the balloon.

12. The catheter system of claim 1 wherein the first electrode is positioned within the balloon interior.

13. The catheter system of claim 1 further comprising an inflation conduit through which the balloon fluid is directed into the balloon interior; and wherein the first electrode is positioned within the inflation conduit.

14. The catheter system of claim 1 wherein the energy source is a laser source that provides pulses of laser energy; and wherein the energy guide includes an optical fiber.

15. A catheter system for treating a treatment site within or adjacent to a vessel wall or heart valve within a body of a patient, the catheter system comprising:
   an energy source that generates energy;
   a balloon that is positionable substantially adjacent to the treatment site, the balloon having a balloon wall that defines a balloon interior, the balloon interior being configured to receive a balloon fluid;
   an inflation conduit through which the balloon fluid is directed into the balloon interior;
   an energy guide that is configured to receive energy from the energy source and guide the energy into the balloon interior; and
   an electrical analyzer assembly that is configured to monitor a condition of the balloon during use of the catheter system, the electrical analyzer assembly including (i) a first electrode that is positioned within the inflation conduit, (ii) a second electrode, and (iii) an impedance detector, the impedance detector being electrically coupled to the first electrode and the second electrode, the impedance detector being configured to detect an impedance between the first electrode and the second electrode.

16. The catheter system of claim 15 wherein the second electrode is positioned on skin of the patient.

17. A catheter system for treating a treatment site within or adjacent to a vessel wall or heart valve within a body of a patient, the catheter system comprising: an energy source that generates energy; a balloon that is positionable substantially adjacent to the treatment site, the balloon having a balloon wall that defines a balloon interior, the balloon interior being configured to receive a balloon fluid; a guidewire that is configured to guide positioning of the balloon substantially adjacent to the treatment site; an energy guide that is configured to receive energy from the energy source and guide the energy into the balloon interior; and an electrical analyzer assembly that is configured to monitor a condition of the balloon during use of the catheter system, the electrical analyzer assembly including (i) a first electrode, (ii) a second electrode that is positioned substantially adjacent to the guidewire, and (iii) an impedance detector, the impedance detector being electrically coupled to the first electrode and the second electrode, the impedance detector being configured to detect an impedance between the first electrode and the second electrode.

18. The catheter system of claim 17 wherein the first electrode is positioned in fluid communication with the balloon fluid.

19. A catheter system for treating a treatment site within or adjacent to a vessel wall or heart valve within a body of a patient, the catheter system comprising:
   an energy source that generates energy;
   a balloon that is positionable substantially adjacent to the treatment site, the balloon having a balloon wall that defines a balloon interior, the balloon interior being configured to receive a balloon fluid;
   a guidewire that is configured to guide positioning of the balloon substantially adjacent to the treatment site;
   a guidewire lumen that is configured to move over the guidewire, the guidewire lumen being coupled to the balloon;
   an energy guide that is configured to receive energy from the energy source and guide the energy into the balloon interior; and
   an electrical analyzer assembly that is configured to monitor a condition of the balloon during use of the catheter system, the electrical analyzer assembly including (i) a first electrode, (ii) a second electrode that is positioned within the guidewire lumen, and (iii) an impedance detector, the impedance detector being electrically coupled to the first electrode and the second electrode, the impedance detector being configured to detect an impedance between the first electrode and the second electrode.

20. The catheter system of claim 19 wherein the first electrode is positioned in fluid communication with the balloon fluid.

* * * * *